(12) United States Patent
Smith et al.

(10) Patent No.: US 7,820,419 B2
(45) Date of Patent: Oct. 26, 2010

(54) FERMENTATION PRODUCT PRODUCTION PROCESSES

(75) Inventors: Mads Torry Smith, Raleigh, NC (US); John Ress, Youngsville, NC (US); Kevin S. Wenger, Rolesville, NC (US); Rikke Monica Festersen, Herlev (DK)

(73) Assignee: Novozymes North America Inc., Franklinton, NC (US)

( * ) Notice: Subject to any disclaimer, the term of this patent is extended or adjusted under 35 U.S.C. 154(b) by 198 days.

(21) Appl. No.: 11/814,304

(22) PCT Filed: Feb. 7, 2006

(86) PCT No.: PCT/US2006/006966

§ 371 (c)(1),
(2), (4) Date: Sep. 24, 2007

(87) PCT Pub. No.: WO2006/086792

PCT Pub. Date: Aug. 17, 2006

(65) Prior Publication Data

US 2008/0138871 A1  Jun. 12, 2008

Related U.S. Application Data

(60) Provisional application No. 60/651,001, filed on Feb. 8, 2005.

(51) Int. Cl.
*C12P 7/06* (2006.01)

(52) U.S. Cl. .................................................... 435/161

(58) Field of Classification Search ................ None
See application file for complete search history.

(56) References Cited

U.S. PATENT DOCUMENTS

| 5,231,017 A | 7/1993 | Lantero et al. |
| 7,244,597 B2 * | 7/2007 | Veit et al. .................... 435/161 |
| 7,429,476 B2 * | 9/2008 | Clarkson et al. ............ 435/219 |
| 2004/0091983 A1 | 5/2004 | Veit et al. |
| 2004/0219649 A1 * | 11/2004 | Olsen et al. ................. 435/161 |
| 2005/0026261 A1 | 2/2005 | Otto et al. |

FOREIGN PATENT DOCUMENTS

| CA | 1 143 677 | 3/1983 |
| CN | 1069768 | 3/1993 |
| WO | WO 92/20777 | 11/1992 |

OTHER PUBLICATIONS

Mullins et al., Biomass, vol. 16, pp. 77-87 (1988).
International Search Report received in international application No. PCT/US2006/006966 (Sep. 19, 2006).

* cited by examiner

*Primary Examiner*—Herbert J. Lilling
(74) *Attorney, Agent, or Firm*—Elias Lambiris

(57) ABSTRACT

The present invention relates to a process for producing a fermentation product from starch-containing material, comprising liquefying said starch-containing material with an alpha-amylase; treating with a protease; saccharifying in the presence of a carbohydrate-source generating enzyme; fermenting in the presence of a fermenting organism.

19 Claims, 9 Drawing Sheets

FERMENTATION PRODUCT PRODUCTION PROCESSES

CROSS-REFERENCE TO RELATED APPLICATIONS

This application is a 35 U.S.C. 371 national application of PCT/US2006/006966 filed Feb. 7, 2006, which claims priority or the benefit under 35 U.S.C. 119 of U.S. provisional application No. 60/651,001 filed Feb. 8, 2005, the contents of which are fully incorporated herein by reference.

FIELD OF THE INVENTION

The present invention relates to processes of producing fermentation products, such as ethanol, from starch-containing material, including degradation of the proteins contained in the starch-containing material.

BACKGROUND OF THE INVENTION

A vast number of commercial products that are difficult to produce synthetically may be produced by fermentation. Such products including alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones; and also products commonly used in the consumable alcohol (e.g., beer and wine), dairy (e.g., in the production of yogurt and cheese), leather, and tobacco industries.

Ethanol has widespread application, including, as an industrial chemical, gasoline additive or straight liquid fuel. As a fuel or fuel additive, ethanol dramatically reduces air emissions while improving engine performance. As a renewable fuel, ethanol reduces national dependence on finite and largely foreign fossil fuel sources, while decreasing the net accumulation of carbon dioxide in the atmosphere.

Typically ethanol is produced by liquefying starch-containing material followed by sequential or simultaneous saccharification and fermentation. Liquefaction involves gelatinization of starch simultaneously with or followed by addition of alpha-amylase in order to degrade starch into dextrins. When producing ethanol the liquefied starch-containing material is saccharified. Saccharification is a step in which dextrins are converted to low molecular $DP_{1-3}$ sugars that, e.g., can be converted by a yeast into ethanol.

U.S. Pat. No. 5,231,017A discloses an ethanol production process comprising (a) liquefying raw material in the presence of an alpha-amylase, (b) saccharifying the liquefied mash in the presence of a glucoamylase, (c) fermenting and (d) recovery of the ethanol, wherein a protease is introduced to the liquefied mash during saccharification and/or fermentation.

Canadian Patent 1,143,677 disclose a process of producing ethanol from amylaceous raw stock by hydrolyzing said raw stock material with an amylolytic enzyme and a cellulase preparation derived from a culture of *Trichoderma könagii* comprising a complex of hydrolytic enzymes including $C_1$-enzyme, exoglucanase, endoglucanase, cellobiase, xylanase, beta-glucosidase, protease and a number of amylolytic enzymes.

Mullins et al., "Biomass" 16 (1988) 2, pp. 77-87, demonstrated that addition of alkaline protease to mash results in an increase in amino nitrogen sufficient to support accelerated rates of ethanol fermentation.

There is a need for further improvement of fermentation product production processes.

SUMMARY OF THE INVENTION

In the first aspect the present invention relates to processes of producing fermentation products, such as ethanol, from starch-containing material, comprising (a) liquefying said starch-containing material with an alpha-amylase;
(b) treating with a protease;
(c) saccharifying in the presence of a carbohydrate-source generating enzyme;
(d) fermenting in the presence of a fermenting organism.

The liquefaction and protein degradation in steps (a) and (b) may be carried out simultaneously or sequentially. Also the saccharification and fermentation steps may be carried out simultaneously (SSF) or sequentially.

DESCRIPTION OF THE INVENTION

The present invention relates to processes of producing fermentation products, such as ethanol, from starch-containing material.

The inventors have surprisingly found that significantly faster fermentation rates, higher fermentation yield, a lower glycerol/ethanol relationship, and a lower residual glucose concentration can be obtained by treating liquefied corn mash with a protease before (simultaneous) saccharification and fermentation.

A separate holding step after liquefaction allows optimal temperature and pH conditions for the protease. The initial breakdown of protein in the post liquefaction step releases free amino nitrogen (FAN) that serves as growth factors for the fermenting organism, such as yeast. The release of FAN helps yeast withstand stress from high substrate and product concentrations, thereby lowering glycerol production and increasing ethanol productivity and ethanol yields. The time required at optimum enzyme conditions is only a few hours. For instance, it was found that 2 hours post liquefaction treatment improved the ethanol yield more that 14% compared to corresponding SSF fermentations where no post liquefaction treatment was carried out. The increased productivity greatly outweighs the time spent on post liquefaction treatment.

Figure 1:
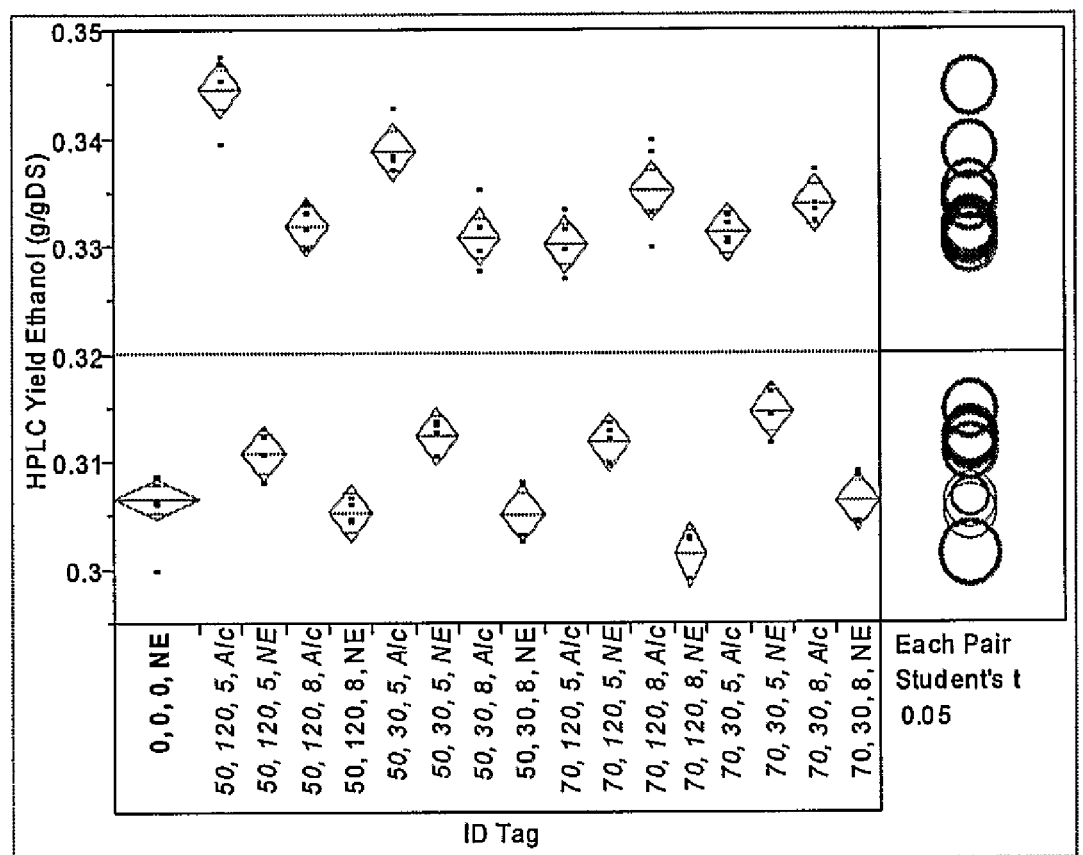
FIG. 1 shows the ethanol yield (g/g DS) after SSF 1) with post liquefaction treatment with Protease ALC (Alc) and 2) without enzyme (NE—No Enzyme), at various temperatures, treatment times and pHs.
Figure 2:
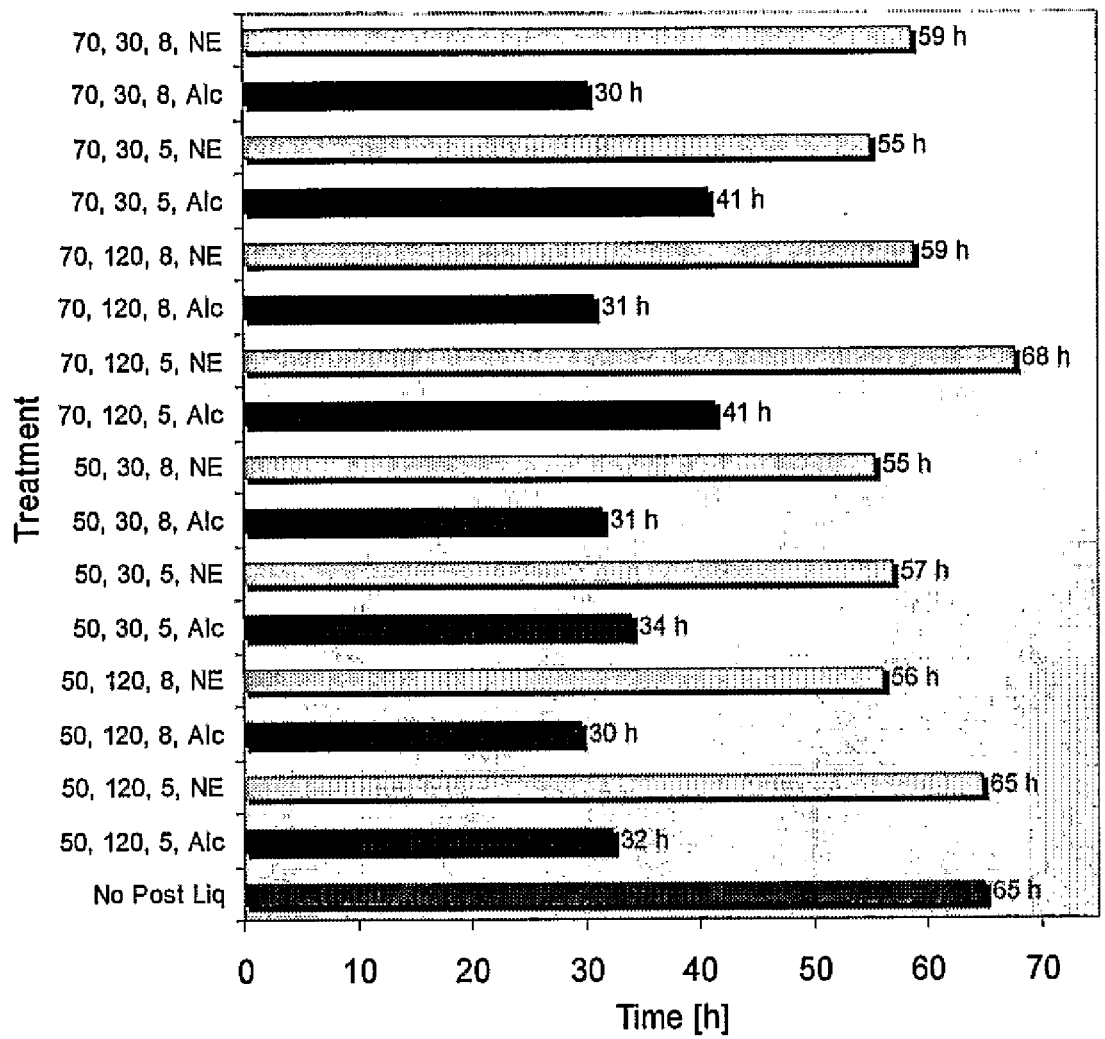
FIG. 2 shows the time it theoretically takes the fermentations to reach the ethanol yield observed in control fermentation without post-liquefaction. Values are based on weight loss per grams of corn mash.
Figure 3:
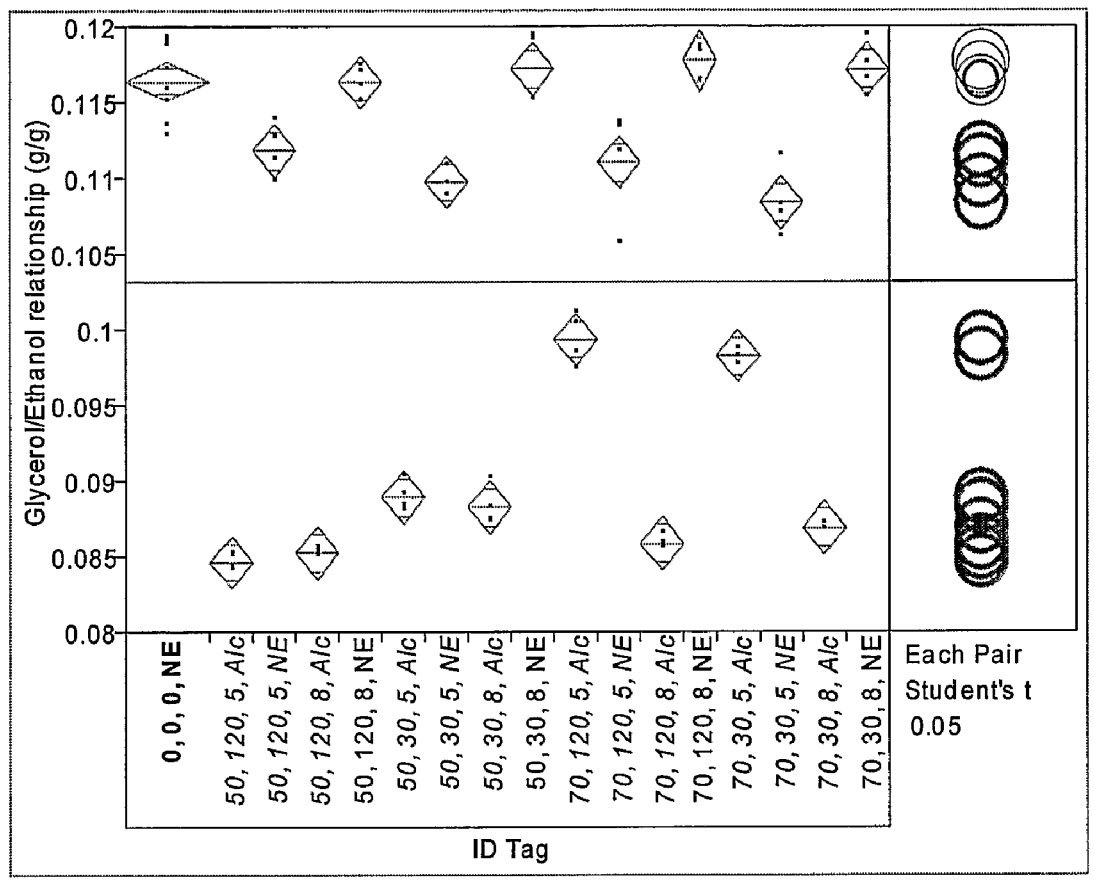
FIG. 3 shows the glycerol/ethanol relationship (g/g) with post liquefaction treatment with Protease ALC (Alc) and 2) without enzyme (NE—No Enzyme), at various temperatures, treatment times and pHs.
Figure 4:
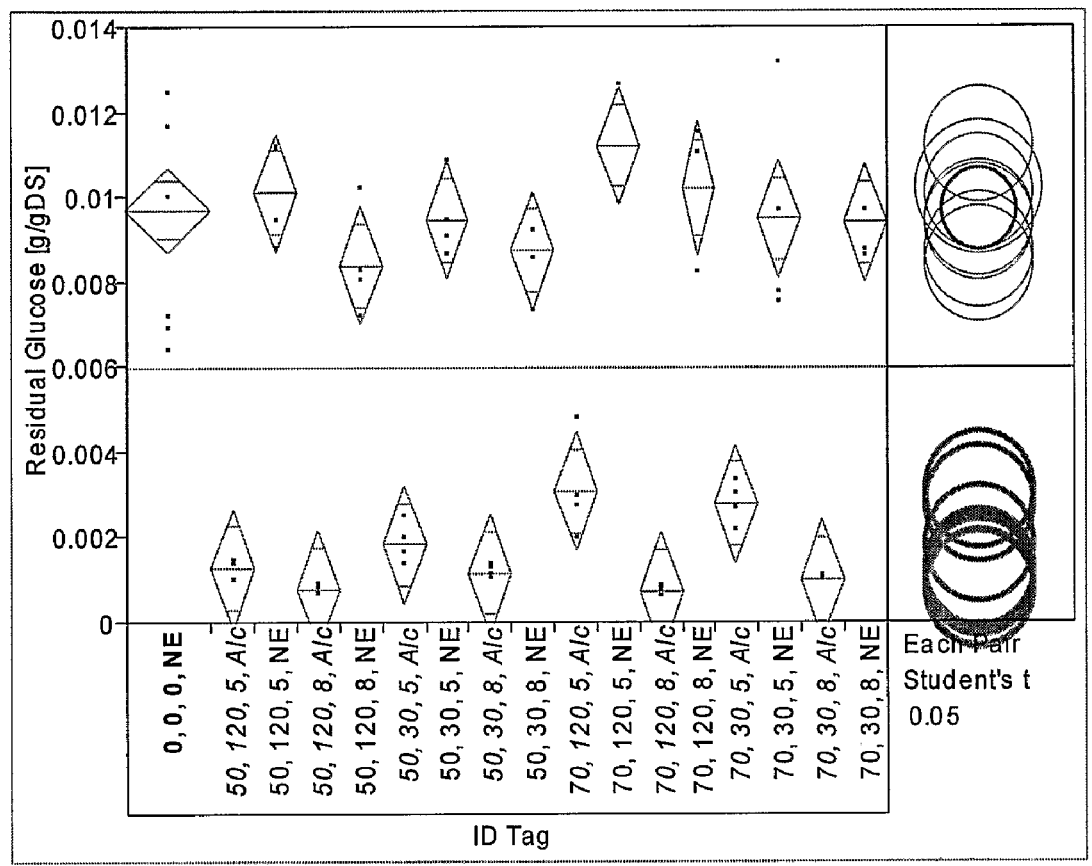
FIG. 4 shows residual glucose [g/gDS] with post liquefaction treatment with Protease ALC (Alc) and 2) without enzyme (NE—No Enzyme), at various temperatures, treatment times and pHs.

In Example 1 (FIG. 2) it is shown that fermentations of post liquefied corn mash with an alkaline protease derived from *Bacillus licheniformis* reaches the ethanol yield of a standard SSF fermentation (i.e., no post liquefaction) in about half the time compared to identical conditions where no protease was present. It was found that both increased treatment times and protease dose increased the overall final yield. However, the increase was most pronounced in the lower doses of protease, i.e., gives the highest response on the yields per amount enzyme added. The response to increased protease dose was found to level off when the concentration approaches 0.1 wt.-% DS. However, it was evident that increased treatment time continued to improve the fermentation performance in the tested time span. Between 7 and 8 hours post liquefaction treatment with a Protease ALC dosage level of 0.007 wt.-% of TS was found to be optimal.

The inventors have also surprisingly found that the protease treatment may advantageously be carried out simultaneously with liquefaction. This is illustrated in Example 2. It is believed that the protein matrix in corn flour stabilizes the protease as opposed to cooked corn mash where the proteins are precipitated. The inventors found that even relatively short protease treatment periods were sufficient. Thus protein degradation is not the time limiting factor for simultaneously liquefaction and protein degradation. It is rather the ability of the alpha-amylase to act on the starch containing material.

Processes for Producing Fermentation Products from Starch-Containing Material

The invention relates to a process for producing a fermentation product, especially ethanol, from starch-containing material, which process includes sequential or simultaneous liquefaction, protein degradation, saccharification, and fermentation steps.

In this aspect the invention relates to a process for producing a fermentation product from starch-containing material comprising the steps of:

(a) liquefying said starch-containing material with an alpha-amylase;

(b) treating with a protease;

(c) saccharifying in the presence of a carbohydrate-source generating enzyme;

(d) fermenting in the presence of a fermenting organism.

In an embodiment the process of the invention further comprises a step (e) of recovering the fermentation product, such as ethanol, preferably by distillation.

Liquefaction—Step (a)

According to the present invention step (a) is a liquefaction step. Liquefaction is a process step in which starch-containing material, preferably milled (whole) grain, is broken down (hydrolyzed) into maltodextrins (dextrins). Liquefaction is typically carried out using an alpha-amylase or by other means known in the art to provide such effect (e.g., acid hydrolysis). Preferred alpha-amylases are of bacterial or fungal origin. The alpha-amylase may be used in an amount between 0.0005-5 KNU per g DS (Dry Solids), preferably between 0.001-1 KNU per g DS, such as around 0.050 KNU per g DS. Suitable examples of alpha-amylases can be found in the "Alpha-Amylase"-section below. The pH during liquefaction may be between about 4.5 and 7, preferably between 5 and 6, preferably around 5.4 or 5.6.

The starting material may be any starch-containing plant material. Preferred are milled whole grains, especially corn, wheat and milo. Examples of contemplated starch-containing materials can be found in the "Starch-containing materials"-section below.

In a particular embodiment, the process of the invention further comprises, prior to step (a), the steps of:

i) milling of starch-containing material;

ii) forming a slurry comprising the milled starch-containing material and water.

The aqueous slurry may contain from 10-50 wt-%, preferably 20-40 wt-%, especially 25-35 wt.-% starch-containing material. The slurry is heated to above the initial gelatinization temperature and alpha-amylase may be added to initiate liquefaction (thinning).

The term "initial gelatinization temperature" means the lowest temperature at which gelatinization of the starch commences. Starch heated in water begins to gelatinize between 55° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein. S. and Lii. C., Starch/Stärke, Vol. 44 (12) pp. 461-466 (1992).

The slurry may in an embodiment be jet-cooked to further gelatinize the slurry before being subjected to alpha-amylase in step (a) of the invention.

More specifically liquefaction may be carried out as a three-step hot slurry process. The slurry is heated to between 60-95° C., preferably 65-90° C., and alpha-amylase (typically around ⅓ of the total dose) may be added to initiate liquefaction (thinning). Then the slurry may be jet-cooked at a temperature between 95-140° C., preferably 105-125° C., for 1-15 minutes, preferably for 3-10 minute, especially around 5 minutes. The slurry is then cooled to 60-95° C., preferably 80-90° C., and more alpha-amylase (typically around ⅔ of the total dose) is added to finalize hydrolysis (secondary liquefaction). The liquefaction step is usually carried out at pH 4.5-6.5, in particular at a pH between 5 and 6. Milled and liquefied whole grains are known as mash.

Post Liquefaction—Step (b)

After liquefaction protease treatment is taking place, preferably at conditions suitable, preferably optimal, for the protease in question. This would typically mean that the temperature during protease treatment in step (b) would be in the range from between 25-90° C., preferably 30-80° C., preferably between 45° C. and 65° C. or 65° C. and 75° C., especially around 50° C. or 70° C., and the pH would be in the range from 2 to 10. For acid proteases the pH during step (b) would be between 2 and 7. For neutral protease the pH during step (b) would be between 5 and 8. For alkaline protease the pH during step (b) would be between 7 and 10. However, a person skilled in the art can easily determine optimal conditions for carrying out the post liquefaction step. The liquefied starch in step (b) may have a concentration in the range between 20 and 50 wt.-% of Total Solids (TS), preferably between 30-40 wt.-% of TS. The protease treatment may take from 0.1 to 12 hours, preferably 1 to 10 hours, especially 2 to 8 hours. The protease may be present in concentrations in the range from 0.0001 to 1.0 wt.-% of TS, preferably 0.001 to 0.1 wt.-% of TS. The protease may be of any origin. Preferred proteases are of fungal, bacterial or plant origin and may be acidic, neutral or alkaline. Examples of suitable proteases can be found in the "Proteases"-section below.

Simultaneous Liquefaction and Protein Degradation

In a preferred embodiment protein degradation is carried out simultaneously with liquefying the starch-containing material. In other words, step (a) and step (b) may be carried out simultaneously. The temperature during protease treatment depends on the enzymes used, but may be in the range from 25-90° C., preferably 30-80° C., such as from 65-75° C., especially around 50° or 70° C. If the protease and alpha-amylase used are heat stable, temperatures in the higher ranges may be used. The preferred pH depends on the enzymes used as indicated above in the "Liquefaction" section, but is according to the invention preferably between pH 4-7, in particular 5-6. It is the required liquefaction time that determines what is a suitable time period for carrying out simultaneous liquefaction and protein degradation according to the invention. Therefore, simultaneous liquefaction and protein degradation may according to the invention be carried for a period of 0.1 to 12 hours, preferably 1 to 10 hours, especially 2 to 8 hours. It should be understood that degradation of protein contained in the starch-containing material may be initiated (by addition of protease) at any time during liquefaction, such as for instance to the aqueous slurry prior to step (a).

Saccharification—Step (c) and Fermentation—Step (d)

"Saccharification" is a process in which maltodextrins (such as post liquefied starch-containing material) is converted to low molecular sugars, such as $DP_{1-3}$ sugars.

The saccharification in step (c) may be carried out using conditions well know in the art.

Saccharification is carried out in the presence of the carbohydrate-source generating enzyme. Examples of carbohydrate-source generating enzymes are glucoamylase, maltogenic amylase, beta-amylase, and a combination thereof. The carbohydrate-source generating enzyme(s), preferably a glucoamylase, is(are) preferably present in a concentration of 0.005-5 AGU/g DS, more preferably between 0.01-1 AGU/g DS, such as especially around 0.1-0.5 AGU/g DS. Examples of carbohydrate-source generating enzymes can be found in the ENZYMES"-section below and include glucoamylases derived from a strain of genera such as *Aspergillus, Talaromyces*, and *Athelia*.

For instance, a full saccharification process may lasts from about 20 to 100 hours, preferably 24 to about 72 hours.

It is common only to do a pre-saccharification of typically 40-90 minutes at a temperature between 30-65° C., typically about 60° C., followed by complete saccharification during fermentation. The pH during saccharification is typically in the range between 4 and 6, normally at about pH 4.5-5.5.

The fermentation step (d) is carried out in the presence of a fermenting organism. The choice of fermenting organism depends on to product to be produced. A person skilled in the art can easily select a suitable fermenting organism. In the case of ethanol production the fermenting organism is yeast, preferably a strain of *Saccharomyces*, especially a strain of *Saccharomyces cerevisiae*. Suitable fermenting organisms are mentioned in the "Fermenting Organisms"-section below.

In a preferred embodiment the saccharification and fermentation steps are combined to a simultaneous saccharification and fermentation (SSF) process, in which there is no holding stage for the saccharification, meaning that fermenting organism, such as yeast, and enzyme(s) may be added together. As mention above it is common to include a pre-saccharification step prior to SSF. A SSF process is typically carried out for between 20 and 100 hours, preferably about 24 to 72 hours, and at a temperature that is optimal for the fermenting organism. In case of ethanol production the SSF process may be carried out at a temperature between 28 and 34° C., preferably around 32° C. The pH during fermentation may be between 3 and 6, preferably pH 4-5.

In accordance with the present invention the fermentation step includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. Preferred fermentation processes include alcohol fermentation processes, as are well known in the art. Preferred fermentation processes are anaerobic fermentation processes, as are well known in the art.

Starch-Containing Material

The starch-containing material used according to the present invention may be any starch-containing plant material. Preferred are starch-containing materials selected from the group consisting of: tubers, roots and whole grains; and any combinations thereof. In an embodiment, the starch-containing material is obtained from cereals. The starch-containing material may, e.g., be selected from the groups consisting of corn (maize), cob, wheat, barley, cassava, sorghum, rye, milo and potato; or any combination thereof.

When the fermentation product is ethanol the starch-containing material is preferably whole grains or at least mainly whole grains. The raw material may also consist of or comprise a side-stream from starch processing, e.g., $C_6$ carbohydrate containing process streams that are not suited for production of syrups.

Milling

In a preferred embodiment of the invention the starch-containing material is reduced in size by, e.g., milling before step (a) in order to open up the structure and allowing for further processing. Two processes of milling are typically used: wet and dry milling. The term "dry milling" denotes milling of the whole grains. In dry milling whole kernels are milled and used in the remaining part of the process. Wet milling gives a good separation of germ and meal (starch granules and protein) and is with a few exceptions applied at locations where there is a parallel production of syrups. Dry milling is preferred in processes aiming at producing ethanol.

The term "grinding" is also understood as milling. In a preferred embodiment of the invention dry milling is used. Other size reducing technologies such as emulsifying technology, rotary pulsation may also be used.

Fermenting Organisms

The term "fermenting organism" refers to any organism capable of providing the desired fermentation product. Suitable fermenting organisms are according to the invention capable of fermenting, i.e., converting, preferably $DP_{1-3}$ sugars, such as especially glucose and maltose, directly or indirectly into the desired fermentation product, such as ethanol. Examples of fermenting organisms include fungal organisms, such as yeast. Preferred yeast includes strains of *Saccharomyces* spp., and in particular *Saccharomyces cerevisiae*. Commercially available yeast includes, e.g., RED STAR™/ Lesaffre, ETHANOL RED™ (available from Red Star/Lesaffre, USA), FALI (available from Fleischmann's Yeast, a division of Burns Philp Food Inc., USA), SUPERSTART (available from Alltech), GERT STRAND (available from Gert Strand AB, Sweden) and FERMIOL™ (available from DSM Specialties).

Yeast cells are preferably applied in amounts of $10^5$ to $10^{12}$, preferably from $10^7$ to $10^{10}$, especially $5 \times 10^7$ viable yeast count per mL of fermentation broth. During ethanol producing phase the yeast cell count should preferably be in the range from $10^7$ to $10^{10}$, especially around $2 \times 10^8$. Further guidance in respect of using yeast for fermentation can be found in, e.g., "The alcohol Textbook" (Editors K. Jacques, T. P. Lyons and D. R. Kelsall, Nottingham University Press, United Kingdom 1999), which is hereby incorporated by reference.

Enzymes

Protease

According to the present invention the starch-containing material may be treated with a protease of any origin. Addition of protease(s) increase(s) the FAN (Free amino nitrogen) level and increases the rate of metabolism of the fermenting organism, such as yeast, and further gives higher fermentation efficiency. According to the invention a peptidase and other protein degrading enzymes are referred to as proteases. In a preferred embodiment the protease is an endo-protease and/or an exo-protease.

Suitable proteases may be of fungal, bacterial, including filamentous fungi and yeast, and plant origin.

In an embodiment the protease is an acidic protease, i.e., a protease characterized by the ability to hydrolyze proteins under acidic conditions below pH 7, e.g., at a pH between 2-7. In an embodiment the acidic protease has an optimum pH in the range from 2.5 and 3.5 (determined on high nitrogen casein substrate at 0.7% w/v at 37° C.) and a temperature optimum between 5 to 50° C. at an enzyme concentration of 10 mg/mL at 30° C. for one hour in 0.1 M piperazine/acetate/ glycine buffer).

In another embodiment the protease is an alkaline protease, i.e., a protease characterized by the ability to hydrolyze proteins under alkaline conditions above pH 7, e.g., at a pH between 7-11. In an embodiment the alkaline protease is derived from a strain of *Bacillus*, preferably *Bacillus licheniformis*. In an embodiment the alkaline protease has an optimum temperature in the range from 7 and 11 and a temperature optimum around 70° C. determined at pH 9.

In another embodiment the protease is a neutral protease, i.e., a protease characterized by the ability to hydrolyze proteins under conditions between pH 5 and 8. In an embodiment the alkaline protease is derived from a strain of *Bacillus*, preferably *Bacillus amyloliquefaciens*. In an embodiment the alkaline protease has an optimum pH in the range between 7 and 11 (determined at 25° C., 10 minutes reaction time with an enzyme concentration of 0.01-0.2 AU/L) and a temperature optimum between 50° C. and 70° C. (determined at pH 8.5, 10 minutes reaction time and 0.03-0.3 AU/L enzyme concentration.

In an embodiment the protease is a metalloprotease. In a preferred embodiment the protease is derived from a strain of the genus *Thermoascus*, preferably a strain of *Thermoascus aurantiacus*, especially *Thermoaccus aurantiacus* CGMCC No. 0670 having the sequence shown in the mature part of SEQ ID NO: 2 in WO 03/048353 hereby incorporated by reference. The *Thermoaccus aurantiacus* protease is active from 20-90° C., with an optimum temperature around 70° C. Further, the enzyme is activity between pH 5-10 with an optimum around pH 6.

Suitable plant proteases may be derived from barley.

Suitable bacterial proteases include *Bacillus* proteases derived from *Bacillus amyloliquefaciens* and *Bacillus licheniformis*. Suitable filamentous bacterial proteases may be derived from a strain of *Nocardiopsis*, preferably *Nocardiopsis prasina* NRRL 18262 protease (or *Nocardiopsis* sp. 10R) and *Nocardiopsis dassonavilla* NRRL 18133 (*Nocardiopsis dassonavilla* M58-1) both described in WO 1988/ 003947 (Novozymes).

Suitable acid fungal proteases include fungal proteases derived from *Aspergillus, Mucor, Rhizomucor, Rhizopus, Candida, Coriolus, Endothia, Enthomophtra, Irpex, Penicillium, Sclerotium, Thermoaccus,* and *Torulopsis*. Especially contemplated are proteases derived from *Aspergillus niger* (see, e.g., Koaze et al., (1964), Agr. Biol. Chem. Japan, 28, 216), *Aspergillus saitoi* (see, e.g., Yoshida, (1954) J. Agr. Chem. Soc. Japan, 28, 66), *Aspergillus awamori* (Hayashida et al., (1977) Agric. Biol. Chem., 42(5), 927-933, *Aspergillus aculeatus* (WO 95/02044), or *Aspergillus oryzae*; proteases from *Mucor pusillus* or *Mucor miehei* disclosed in U.S. Pat. No. 4,357,357 and U.S. Pat. No. 3,988,207; and *Rhizomucor mehei* or *Rhizomucor pusillus* disclosed in, e.g., WO 94/24880 (hereby incorporated by reference).

Aspartic acid proteases are described in, for example, Hand-book of Proteolytic Enzymes, Edited by A. J. Barrett, N. D. Rawlings and J. F. Woessner, Aca-demic Press, San Diego, 1998, Chapter 270). Suitable examples of aspartic acid protease include, e.g., those disclosed in R. M. Berka et al. Gene, 96, 313 (1990)); (R. M. Berka et al. Gene, 125, 195-198 (1993)); and Gomi et al. Biosci. Biotech. Biochem. 57, 1095-1100 (1993), which are hereby incorporated by reference.

Commercially available products include ALCALASE®, ESPERASE™, NEUTRASE®, RENILASE®, NOVOZYM™ FM 2.0L, and NOVOZYM™ 50006 (available from Novozymes A/S, Denmark) and GC106™ and SPEZYME™ FAN from Genencor Int., Inc., USA.

The protease may be present in concentrations in the range from 0.0001 to 1.0 wt.-% of TS, preferably 0.001 to 0.1 wt.-% of TS.

Alpha-Amylase

The alpha-amylase may according to the invention be of any origin. Preferred are alpha-amylases of fungal or bacterial origin.

In a preferred embodiment the alpha-amylase is an acid alpha-amylase, e.g., fungal acid alpha-amylase or bacterial acid alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases

According to the invention a bacterial alpha-amylase may preferably be derived from the genus *Bacillus*.

In a preferred embodiment the *Bacillus* alpha-amylase is derived from a strain of *B. licheniformis, B. amyloliquefaciens, B. subtilis* or *B. stearothermophilus,* but may also be derived from other *Bacillus* sp. Specific examples of contemplated alpha-amylases include the *Bacillus licheniformis* alpha-amylase (BLA) shown in SEQ ID NO: 4 in WO 99/19467, the *Bacillus amyloliquefaciens* alpha-amylase (BAN) shown in SEQ ID NO: 5 in WO 99/19467, and the *Bacillus stearothermophilus* alpha-amylase (BSG) shown in SEQ ID NO: 3 in WO 99/19467. In an embodiment of the invention the alpha-amylase is an enzyme having a degree of identity of at least 60%, preferably at least 70%, more preferred at least 80%, even more preferred at least 90%, such as at least 95%, at least 96%, at least 97%, at least 98% or at least 99% identity to any of the sequences shown as SEQ ID NOS: 1, 2, 3, 4, or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. Nos. 6,093,562, 6,297,038 or U.S. Pat. No. 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta(181-182) compared to the wild-type BSG alpha-amylase amino acid sequence set forth in SEQ ID NO:3 disclosed in WO 99/19467 or deletion of amino acids R179 and G180 using SEQ ID NO:3 in WO 99/19467 for numbering (which reference is hereby incorporated by reference). Even more preferred are *Bacillus* alpha-amylases, especially *Bacillus stearothermophilus* alpha-amylase, which have a double deletion corresponding to delta(181-182) and further comprise a N193F substitution (also denoted I181*+G182*+N193F) compared to the wild-type BSG alpha-amylase amino acid sequence set forth in SEQ ID NO:3 disclosed in WO 99/19467.

The alpha-amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic alpha-amylase from *Bacillus stearothermophilus* strain NCIB 11837 is commercially available from Novozymes A/S, Denmark. The maltogenic alpha-amylase is described in U.S. Pat. Nos. 4,598,048, 4,604,355 and 6,162,628, which are hereby incorporated by reference.

Bacterial Hybrid Alpha-Amylases

A hybrid alpha-amylase specifically contemplated comprises 445 C-terminal amino acid residues of the *Bacillus licheniformis* alpha-amylase (shown as SEQ ID NO: 4 in WO 99/19467) and the 37 N-terminal amino acid residues of the alpha-amylase derived from *Bacillus amyloliquefaciens* (shown as SEQ ID NO: 3 in WO 99/194676), with one or more, especially all, of the following substitution:

G48A+T49I+G107A+H156Y+A181T+N190F+I201F+A209V+Q264S (using the *Bacillus licheniformis* numbering). Also preferred are variants having one or more of the following mutations (or corresponding mutations in other *Bacillus* alpha-amylase backbones): H154Y, A181T, N190F, A209V and Q264S and/or deletion of two residues between positions 176 and 179, preferably deletion of E178 and G179 (using the SEQ ID NO: 5 numbering of WO 99/19467).

The bacterial alpha-amylase may be added in amounts as are well-known in the art. When measured in KNU units (described below in the Materials & Methods"-section) the alpha-amylase activity is preferably present in an amount of 0.0005-5 KNU per g DS, preferably between 0.001-1 KNU per g DS, such as around 0.050 KNU per g DS.

Fungal Alpha-Amylases

Fungal acid alpha-amylases include acid alpha-amylases derived from a strain of the genus *Aspergillus*, such as *Aspergillus oryzae, Aspergillus niger* or *Aspergillus kawachii*.

A preferred acid fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

Other contemplated wild-type alpha-amylases include those derived from a strain of the genera *Rhizomucor* and *Meripilus*, preferably a strain of *Rhizomucor pusillus* or *Meripilus giganteus*.

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid fungal alpha-amylase is derived from a strain of *Aspergillus kawachii*, e.g., the one disclosed by Kaneko et al. J. Ferment. Bioeng. 81:292-298(1996) "Molecular-cloning and determination of the nucleotide-sequence of a gene encoding an acid-stable alpha-amylase from *Aspergillus kawachii*."; and further as EMBL:#AB008370.

Fungal Hybrid Alpha-Amylase

In an embodiment the fungal alpha-amylase is a hybrid alpha-amylase. Preferred examples of fungal hybrid alpha-amylases include the ones disclosed in WO 2005/003311 or U.S. Patent Publication No. 2005/0054071 (Novozymes) or U.S. patent application No. 60/638,614 (Novozymes) which are hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 in the examples in co-pending U.S. patent application No. 60/638,614, including Fungamyl variant with catalytic domain JA118 and *Athelia rolfsii* SBD (SEQ ID NO:100 in U.S. application 60/638, 614), *Rhizomucor pusillus* alpha-amylase with *Athelia rolfsii* AMG linker and SBD (SEQ ID NO:101 in U.S. 60/638,614) and *Meripilus giganteus* alpha-amylase with *Athelia rolfsii* glucoamylase linker and SBD (SEQ ID NO:102 in U.S. 60/638,614).

Other specific examples of contemplated hybrid alpha-amylases include those disclosed in U.S. Patent Publication No. 2005/0054071, including those disclosed in Table 3 on page 15, such as *Aspergillus niger* alpha-amylase with *Aspergillus kawachii* linker and starch binding domain.

Commercial Alpha-Amylase Products

Preferred commercial compositions comprising alpha-amylase include MYCO-LASE™ (DSM, Holland), BAN™, TERMAMYL™ SC, FUNGAMYL™, LIQUOZYME™ X and SAN™ SUPER, SAN™ EXTRA L (Novozymes A/S) and CLARASE™ L-40,000, DEX-LO™, SPEZYME™ FRED, SPEZYME™ ETHYL, SPEZYME™ AA, and SPEZYME™ DELTA AA (Genencor Int.), and the acid fungal alpha-amylase sold under the trade name SP288 (available from Novozymes A/S, Denmark).

An acid alpha-amylases may according to the invention be added in an amount of 0.1 to 10 AFAU/g DS, preferably 0.10 to 5 AFAU/g DS, especially 0.3 to 2 AFAU/g DS.

Carbohydrate-Source Generating Enzyme

The term "carbohydrate-source generating enzyme" includes glucoamylase (being glucose generators), beta-amylase and maltogenic amylase (being maltose generators). A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Especially contemplated mixtures are mixtures of at least a glucoamylase and an alpha-amylase, especially an acid amylase, even more preferred an acid fungal alpha-amylase. The ratio between acidic fungal alpha-amylase activity (AFAU) per glucoamylase activity (AGU) (AFAU per AGU) may in an embodiment of the invention be at least 0.1, in particular at least 0.16, such as in the range from 0.12 to 0.50 or more.

Glucoamylase

A glucoamylase used according to the invention may be derived from any suitable source, e.g., derived from a microorganism or a plant. Preferred glucoamylases are of fungal or bacterial origin, e.g., selected from the group consisting of *Aspergillus* glucoamylases, in particular *A. niger* G1 or G2 glucoamylase (Boel et al. (1984), EMBO J. 3 (5), p. 1097-1102), or variants thereof, such as one disclosed in WO 92/00381, WO 00/04136, WO 01/04273 and WO 03/029449 (from Novozymes, Denmark, hereby incorporated by reference); the *A. awamori* glucoamylase (WO 84/02921), *A. oryzae* (Agric. Biol. Chem. (1991), 55 (4), p. 941-949), or variants or fragments thereof.

Other *Aspergillus* glucoamylase variants include variants to enhance the thermal stability: G137A and G139A (Chen et al. (1996), Prot. Eng. 9, 499-505); D257E and D293E/Q (Chen et al. (1995), Prot. Engng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Engng. 10, 1199-1204. Other glucoamylases include *Athelia rolfsii* (previously denoted *Corticium rolfsii*) glucoamylase (see U.S. Pat. No. 4,727,026 and (Nagasaka, Y. et al. (1998) Purification and properties of the raw-starch-degrading glucoamylases from *Corticium rolfsii*, Appl Microbiol Biotechnol 50:323-330), *Talaromyces* glucoamylases, in particular, derived from *Talaromyces emersonii* (WO 99/28448), *Talaromyces leycettanus* (U.S. Pat. No. Re. 32,153), *Talaromyces duponti*, *Talaromyces thermophilus* (U.S. Pat. No. 4,587,215). Bacterial glucoamylases contemplated include glucoamylases from the genus *Clostridium*, in particular *C. thermoamylolyticum* (EP 135,138), and *C. thermohydrosulfuricum* (WO 86/01831).

Other glucoamylases contemplated include glucoamylases from a strain of the genus *Trametes*, preferably a strain of *Trametes cingulata* disclosed in co-pending U.S. provisional application No. 60/650,612 filed Feb. 7, 2005 (which is hereby incorporated by reference).

In another embodiment the glucoamylase is a hybrid enzyme, preferably including a catalytic domain of fungal origin. The catalytic domain may be derived from a strain of *Aspergillus*, preferably from a strain of *Aspergillus niger* or *Aspergillus oryzae*; *Athelia*, preferably *Athelia rolfsii*; *Talaromyces*, preferably *Talaromyces emersonii*. In a preferred embodiment hybrid glucoamylase comprises a carbohydrate-binding module of fungal origin, such as derived from a strain of *Aspergillus*, *Aspergillus kawachii* alpha-amylase, or derived from *Aspergillus niger* glucoamylase, or derived from *Athelia* sp. glucoamylase, preferably from *Athelia rolfsii* glucoamylase.

In a preferred embodiment the hybrid glucoamylase is one disclosed in WO 2005/045018 (hereby incorporated by reference).

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylase may in an embodiment be added in an amount of 0.005-2 AGU/g DS, preferably between 0.01-1 AGU/g DS, such as especially around 0.3 AGU/g DS.

Beta-Amylase

At least according to the invention the a beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (W. M. Fogarty and C. T. Kelly, Progress in Industrial Microbiology, vol. 15, pp. 112-115, 1979). These beta-amylases are characterized by having optimum temperatures in the range from 40° C. to 65° C. and optimum pH in the range from 4.5 to 7. A commercially available beta-amylase from barley is NOVOZYM™ WBA from Novozymes A/S, Denmark and SPEZYME™ BBA 1500 from Genencor Int., USA.

Maltogenic Amylase

The amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference.

The maltogenic amylase may in a preferred embodiment be added in an amount of 0.05-5 mg total protein/gram DS or 0.05-5 MANU/g DS.

Even if not specifically mentioned in context of a process of the invention, it is to be understood that the enzyme(s) is(are) used in an "effective amount".

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The present invention is further described by the following examples which should not be construed as limiting the scope of the invention.

Materials and Methods

Enzymes

Protease ALC: Wild-type alkaline protease derived from *Bacillus licheniformis*.

Glucoamylase T: Glucoamylase derived from *Talaromyces emersonii* and disclosed as SEQ ID NO: 7 in WO 99/28448.

Alpha-Amylase A: *Bacillus stearothermophilus* alpha-amylase variant with the mutations: I181*+G182*+N193F disclosed in U.S. Pat. No. 6,187,576 and available on request from Novozymes A/S, Denmark.

Peptidase A is a clan AA-peptidase family A1 enzyme derived from *Rhizomucor miehei* and produced recombinantly in *Aspergillus oryzae*. The enzyme is available on request from Novozymes A/S, Denmark.

Yeast

RED STAR™ available from Red Star/Lesaffre, USA

Methods

Alpha-Amylase Activity (KNU)

The amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Determination of FAU Activity

One Fungal Alpha-Amylase Unit (FAU) is defined as the amount of enzyme, which breaks down 5.26 g starch (Merck Amylum solubile Erg. B.6, Batch 9947275) per hour based upon the following standard conditions:

| Substrate | Soluble starch |
|---|---|
| Temperature | 37° C. |
| pH | 4.7 |
| Reaction time | 7-20 minutes |

Determination of Acid Alpha-Amylase Activity (AFAU)

Acid alpha-amylase activity is measured in AFAU (Acid Fungal Alpha-amylase Units), which are determined relative to an enzyme standard.

The standard used is AMG 300 L (from Novozymes A/S, Denmark, glucoamylase wild-type *Aspergillus niger* G1, also disclosed in Boel et al. (1984), EMBO J. 3 (5), p. 1097-1102) and WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method, 1 AFAU is defined as the amount of enzyme, which degrades 5.260 mg starch dry matter per hour under standard conditions.

Iodine forms a blue complex with starch but not with its degradation products. The intensity of color is therefore directly proportional to the concentration of starch. Amylase activity is determined using reverse colorimetry as a reduction in the concentration of starch under specified analytic conditions.

| Alpha-amylase | | |
|---|---|---|
| Starch + Iodine | $\rightarrow$ | Dextrins + Oligosaccharides |
| | 40° C., pH 2.5 | |
| Blue/violet | t = 23 sec. | Decoloration |

Standard conditions/reaction conditions: (per minute)

| Substrate: | Starch, approx. 0.17 g/L |
|---|---|
| Buffer: | Citate, approx. 0.03 M |
| Iodine ($I_2$): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | lambda = 590 nm |
| Enzyme concentration: | 0.025 AFAU/mL |
| Enzyme working range: | 0.01-0.04 AFAU/mL |

If further details are preferred these can be found in EB-SM-0259.02/01 available on request from Novozymes A/S, Denmark, and incorporated by reference.

Acid Alpha-Amylase Units (AAU)

The acid alpha-amylase activity can be measured in AAU (Acid Alpha-amylase Units), which is an absolute method. One Acid Amylase Unit (AAU) is the quantity of enzyme converting 1 g of starch (100% of dry matter) per hour under standardized conditions into a product having a transmission at 620 nm after reaction with an iodine solution of known strength equal to the one of a color reference.

Standard Conditions/Reaction Conditions:

| Substrate: | Soluble starch. Concentration approx. 20 g DS/L. |
|---|---|
| Buffer: | Citrate, approx. 0.13 M, pH = 4.2 |
| Iodine solution: | 40.176 g potassium iodide + 0.088 g iodine/L |
| City water | 15°-20°dH (German degree hardness) |
| pH: | 4.2 |
| Incubation temperature: | 30° C. |
| Reaction time: | 11 minutes |
| Wavelength: | 620 nm |
| Enzyme concentration: | 0.13-0.19 AAU/mL |
| Enzyme working range: | 0.13-0.19 AAU/mL |

The starch should be Lintner starch, which is a thin-boiling starch used in the laboratory as calorimetric indicator. Lintner starch is obtained by dilute hydrochloric acid treatment of native starch so that it retains the ability to color blue with iodine. Further details can be found in EP0140410B2, which disclosure is hereby included by reference.

Glucoamylase Activity (AGI)

Glucoamylase (equivalent to amyloglucosidase) converts starch into glucose. The amount of glucose is determined here by the glucose oxidase method for the activity determination. The method described in the section 76-11 Starch—Glucoamylase Method with Subsequent Measurement of Glucose with Glucose Oxidase in "Approved methods of the American Association of Cereal Chemists". Vol. 1-2 AACC, from American Association of Cereal Chemists, (2000); ISBN: 1-891127-12-8.

One glucoamylase unit (AGI) is the quantity of enzyme which will form 1 micro mole of glucose per minute under the standard conditions of the method.

Standard Conditions/Reaction Conditions:

| Substrate: | Soluble starch. Concentration approx. 16 g dry matter/L. |
|---|---|
| Buffer: | Acetate, approx. 0.04 M, pH = 4.3 |
| pH: | 4.3 |
| Incubation temperature: | 60° C. |
| Reaction time: | 15 minutes |
| Termination of the reaction: | NaOH to a concentration of approximately 0.2 g/L (pH~9) |
| Enzyme concentration: | 0.15-0.55 AAU/mL |

The starch should be Lintner starch, which is a thin-boiling starch used in the laboratory as colorimetric indicator. Lintner starch is obtained by dilute hydrochloric acid treatment of native starch so that it retains the ability to color blue with iodine.

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12 M; 0.15 M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Determination of Maltogenic Amylase activity (MANU)

One MANU (Maltogenic Amylase Novo Unit) may be defined as the amount of enzyme required to release one micro mole of maltose per minute at a concentration of 10 mg of maltotriose (Sigma M 8378) substrate per ml of 0.1 M citrate buffer, pH 5.0 at 37° C. for 30 minutes.

EXAMPLES

Example 1

Post Liquefaction Protease Treatment of Corn Mash

The following experiments were carried out in 15 mL test snap-cap tubes using 5 g of corn mash (34 wt.-% g total solids/g):

Alkaline *Bacillus licheniformis* protease (Protease ALC) treatment vs. No Enzyme
Temperature (50° and 70° C.)
Time (0.5 and 2 hours)
pH (5 and 8).

The impact from the protease treatment (post liquefaction treatment) was assessed by conducting a standard SSF fermentation.

Post Liquefaction Treatment: Liquefied corn mash (CM) was divided in 2×500 mL and the pH was adjusted to 5 and 8, respectively, in the two fractions. Before adjusting for pH, samples were taken for total solids (TS) determination. The pH adjusted liquefied CM were distributed (5 mL) into 15 mL test tubes which were divided among four tube racks for each time and temp:

50° C. at 30 minutes,
50° C. at 120 minutes,
70° C. at 30 minutes,
70° C. at 120 minutes.

Protease was added according to the solids content in each tube and the racks were placed in water baths at the required temperature and time. When the post liquefaction treatment was finalized the tubes were cooled down quickly and stored on ice. Before fermentation tubes were adjusted to pH 5 using $H_2SO_4$ (approx 140 microL of 20% $H_2SO_4$).

SSF: Fermentations were carried out as SSF at 32° C., 65 hours, 0.054-% w/w DS Glucoamylase T, pH=5, using RED STAR™ yeast. All tests were run in four replicates and controls were included in the fermentations. The fermentations were monitored by weighing the individual tubes and recording the time and date of the measurement. This data set was then used to calculate the weight loss of each tube over time. At the end of fermentation tubes were sampled for HPLC analysis of sugars and fermentation products. The results are displayed in FIG. 1 to 4. (NE=No Enzyme) (Alc=Protease ALC)

Conclusions

Addition of protease was found to have a significant positive impact on ethanol yields, glycerol production and residual glucose levels. The results showed a significant higher ethanol yield; a significant lower glycerol/ethanol relationship; and significant lower residual glucose concentration for protease post liquefied corn mash treatment.

SSF fermentations using Post Liquefied corn mash reached the yield of the standard SSF control, i.e., without post liquefaction, in significantly less time.

Example 2

Simultaneous Liquefaction and Protein Degradation

To study the effect of conducting starch liquefaction and protein degradation simultaneous, Alpha-Amylase A and Protease ALC and Peptidase A, respectively, were added during liquefaction carried out at 67.5° C. and 70° C., respectively.

Liquefaction: Corn flour was mixed with water to obtain a DS fraction of 34.10 wt. %. pH was adjusted to 5.6 and samples were taken for DS determination. 5 g of this corn slurry was transferred to 15 mL test tubes, which were liquefied using Alpha-Amylase A and Protease ALC and Peptidase A, respectively, for 1 hour after the corn slurry reached the designated liquefaction temperature, which were 67.5° C. and 70° C.

SSF Fermentation: Glucoamylase T was added to all tubes after liquefaction. Fermentations were carried out as SSF at 32° C., 70 hours using RED STAR™ yeast. Yeast was added in about $1 \times 10^7$ cells/mL. All treatments were conducted in 8 replicates and non-liquefied corn slurry controls were included in the fermentation. The fermentations were monitored by weighing the individual tubes and recording the time and date of the measurement. At the end of fermentation tubes were sampled for HPLC analysis of sugars and fermentation products. The primary parameters evaluated were ethanol and glycerol.

TABLE 1

Overview of experiments carried out (DS = dry solids; EP = Enzyme protein)

| Treatment | AGU/g DS | NU/g DS | mg EP/g DS | mg EP/g DS |
|---|---|---|---|---|
| Glucoamylase T | 0.5 | 50 | | |
| Alpha-Amylase A | 0.5 | 50 | | |
| Protease ALC | 0.5 | 50 | 0.02 | |
| Peptidase A | 0.5 | 50 | | 0.02 |

The test results are shown in FIGS. 5-9.

Ethanol

Figure 5:
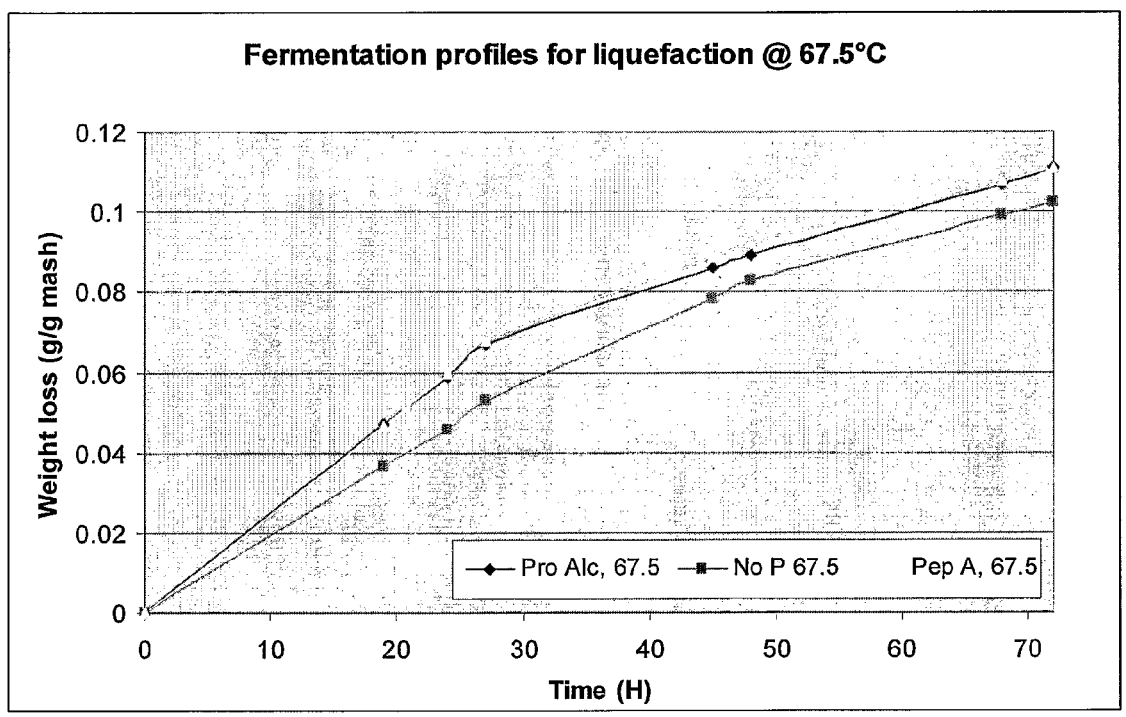
FIG. 5 shows the weight loss profiles for simultaneous liquefaction and protein degradation at 67.5° C. for two proteases compared to a no-protease control as a function of fermentation time.
Figure 6:
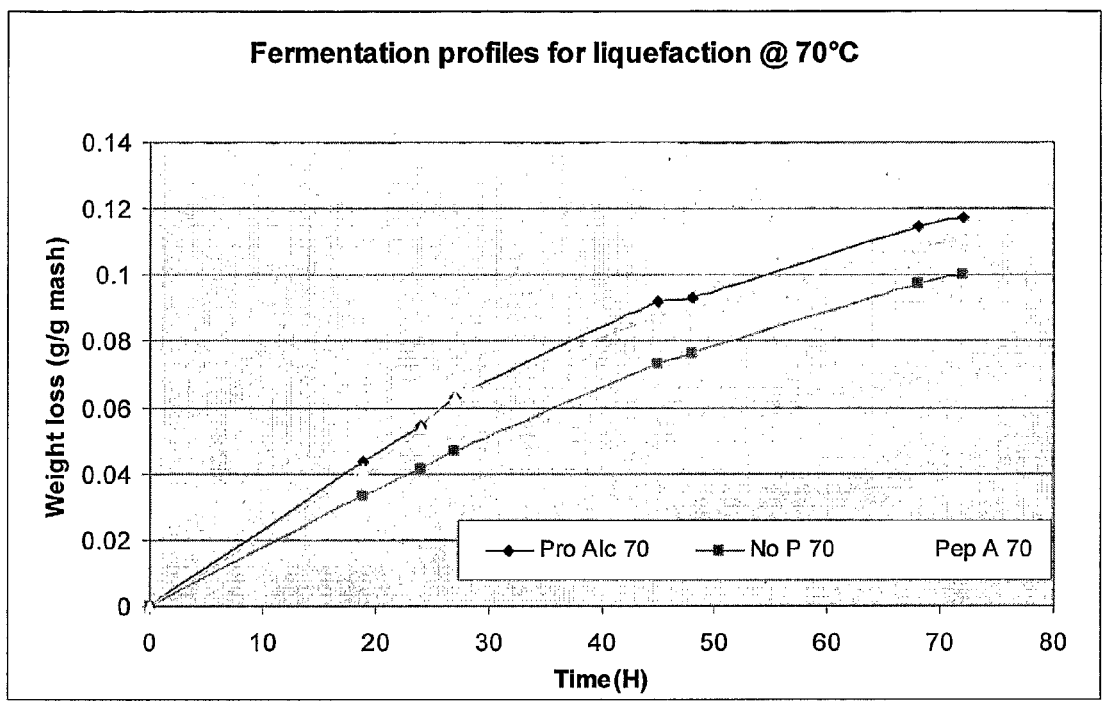
FIG. 6 shows the weight loss profiles for simultaneous liquefaction and protein degradation at 70° C. for two proteases compared to a no-protease control as a function of fermentation time.

FIGS. 5 and 6 show that simultaneous liquefaction and protein degradation with Protease ALC and Peptidase A, respectively, had higher weight loss compared to the blind test (no protease).

Ethanol yields were determined after 24, 48 and 70 hours.

TABLE 2

HPLC ethanol results after 24 and 48 hours fermentation

| Treatment | Ethanol | |
|---|---|---|
| | 24 Hours | 48 hours |
| No Protease - control (67.5° C.) | 0.142 | 0.222 |
| Protease ALC (67.5° C.) | 0.178 | 0.228 |
| Peptidase A (67.5° C.) | 0.179 | 0.230 |
| No Protease - control (70° C.) | 0.138 | 0.217 |
| Protease ALC (70° C.) | 0.178 | 0.250 |
| Peptidase A (70° C.) | 0.168 | 0.243 |

The HPLC results, after 24 and 48 hours, show that simultaneous liquefaction and protein degradation at 67.5° C. and 70° C., respectively, improves the ethanol yield.

Figure 7:
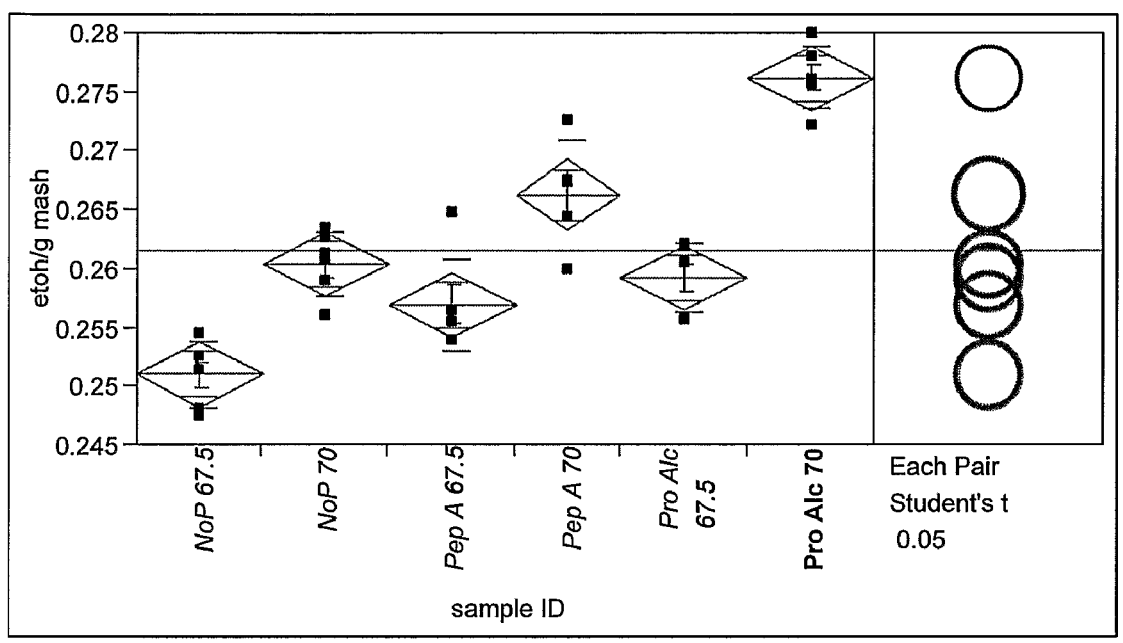
FIG. 7 shows the ethanol yield (g/g DS) after 70 hours fermentation when liquefaction and protein degradation is carried out simultaneously with and without protease at 67.5° C. and 70° C., respectively.

The results show that increased ethanol yield is obtained after 70 hours fermentation when carrying out simultaneous liquefaction and protein degradation (see FIG. 7). (NoP=No protease; Pro Alc=Protease ALC; PEP A=Peptidase A). The ethanol yield after simultaneous liquefaction and protein degradation was higher at 70° C. than at 67.5° C.

Glycerol

Figure 8:
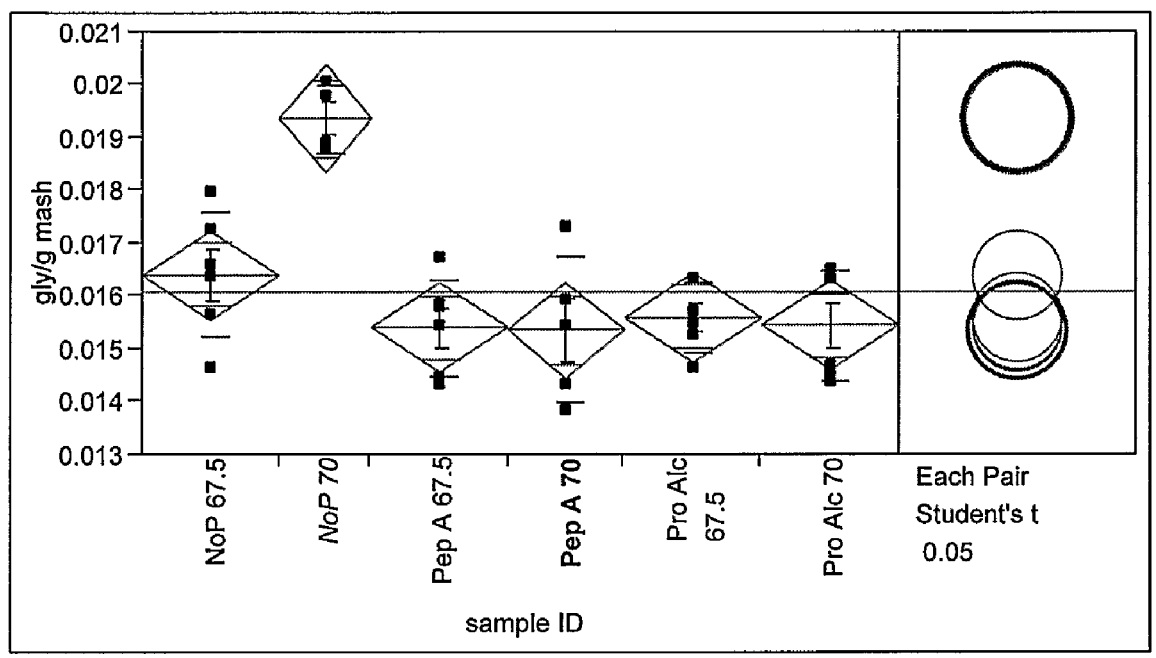
FIG. 8 shows the glycerol level (g/g DS) after 70 hours fermentation when liquefaction and protein degradation is carried out simultaneously with and without protease at 67.5° C. and 70° C., respectively.

The results show that lowered glycerol levels are obtained after 70 hours fermentation when carrying out simultaneous liquefaction and protein degradation (see FIG. 8). (NoP=No protease; Pro Alc=Protease ALC; PEP A=Peptidase A).

Glycerol/Ethanol

Figure 9:
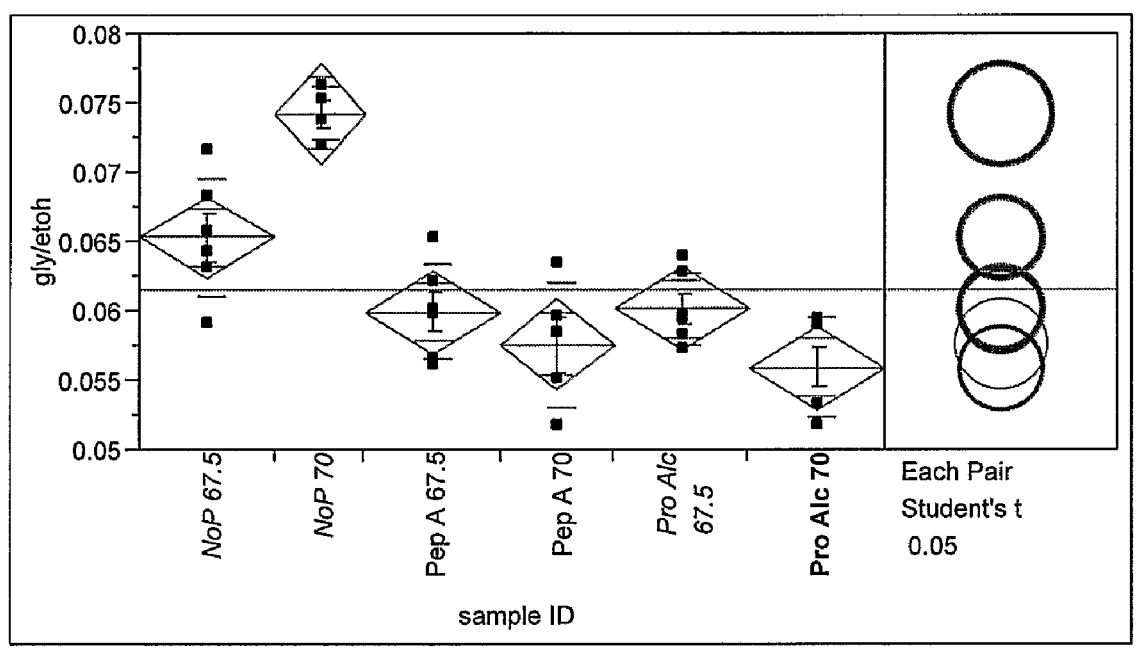
FIG. 9 shows the glycerol/ethanol ratio (g glycerol/g ethanol) after 70 hours fermentation when liquefaction and protein degradation is carried out simultaneously with and without protease at 67.5° C. and 70° C., respectively.

The results show that an improved glycerol/ethanol ratio is obtained after 70 hours fermentation when carrying out simultaneous liquefaction and protein degradation (FIG. 9). (NoP=No protease; Pro Alc=Protease ALC; PEP A=Peptidase A).

The invention claimed is:

1. A process for producing an alcohol from starch-containing material, comprising
    (a) liquefying said starch-containing material with an alpha-amylase;
    (b) treating the liquefied mash from step (a) with a protease before initiating step (c);
    (c) saccharifying in the presence of a carbohydrate-source generating enzyme;
    (d) fermenting in the presence of a fermenting organism to produce the alcohol.

2. The process of claim 1, wherein steps (a) and (b) are carried out simultaneously or sequentially.

3. The process of claim 1, further comprising a step of:
    (e) distillation to obtain the alcohol.

4. The process of claim 1, wherein the alcohol is ethanol.

5. The process of claim 1, wherein step (a) is carried out using a bacterial alpha-amylase or a fungal alpha-amylase.

6. The process of claim 1, wherein the pH during liquefaction is from about 4.5 to 7.

7. The process of claim 1, further comprising, prior to the step (a), the steps of:
    i) milling of starch-containing material;
    ii) forming a slurry comprising the milled starch-containing material and water.

8. The process of claim 7, wherein the slurry is heated to above the initial gelatinization temperature.

9. The process of claim 7, wherein the slurry is jet-cooked at a temperature of 95-140° C. before step (a).

10. The process of claim 1, wherein step (b) is carried out as a post liquefaction protease treatment.

11. The process of claim 1, wherein the protease is a bacterial protease derived from *Bacillus* or *Nocardiopsis*.

12. The process of claim 1, wherein the protease is a plant protease derived from barley.

13. The process of claim 1, wherein step (b) is carried out at conditions optimal for the protease in question.

14. The process of claim 1, wherein the protease treatment in step (b) is carried out at a temperature of 25-90° C.

15. The process of claim 1, wherein the during protease treatment in step (b) is carried out at a pH of 2-11.

16. The process of claim 1, wherein the liquefied starch in step (b) has a concentration of 20-50% (w/w) Total Solids (TS).

17. The process of claim 1, wherein the protease treatment in step (b) is carried out for 0.1 to 12 hours.

18. The process of claim 1, wherein the protease is present at a concentration of 0.0001 to 1 wt.-% of TS.

19. The process of claim 1, wherein the saccharification in step (c) is carried out as a pre-saccharification step lasting for about 40 to 90 minutes, at a temperature of about 28-65° C. and a pH of 4-6, followed by complete saccharification during fermentation in a simultaneous saccharification and fermentation process (SSF).

* * * * *

UNITED STATES PATENT AND TRADEMARK OFFICE
CERTIFICATE OF CORRECTION

PATENT NO. : 7,820,419 B2
APPLICATION NO. : 11/814304
DATED : October 26, 2010
INVENTOR(S) : Mads Torry Smith et al.

It is certified that error appears in the above-identified patent and that said Letters Patent is hereby corrected as shown below:

In the Specification

At Column 1, Line 15, please add the following:
STATEMENT AS TO RIGHTS TO INVENTIONS MADE UNDER FEDERALLY SPONSORED RESEARCH AND DEVELOPMENT
This invention was made with government support under Cooperative Agreement No. 04-03-CA-70759 awarded by the Department of Energy. The Government has certain rights in the invention.

Signed and Sealed this
Eighteenth Day of June, 2019

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 7,820,419 B2 |
| APPLICATION NO. | : 11/814304 |
| DATED | : October 26, 2010 |
| INVENTOR(S) | : Mads Torry Smith et al. |

It is certified that error appears in the above-identified patent and that said Letters Patent is hereby corrected as shown below:

In the Specification

At Column 1, Line 15, please amend as follows:
--This invention was made with government support under Grant No. DE-FC36-03GO13142 awarded by the Department of Energy. The Government has certain rights in the invention.--

This certificate supersedes the Certificate of Correction issued June 18, 2019.

Signed and Sealed this
Thirtieth Day of July, 2019

Andrei Iancu
*Director of the United States Patent and Trademark Office*

(12) INTER PARTES REVIEW CERTIFICATE (3125th)
United States Patent (10) Number: US 7,820,419 K1
Smith et al. (45) Certificate Issued: May 10, 2023

(54) FERMENTATION PRODUCT PRODUCTION PROCESSES

(75) Inventors: Mads Torry Smith; John Ress; Kevin S. Wenger; Rikke Monica Festersen

(73) Assignee: NOVOZYMES NORTH AMERICA, INC.

Trial Number:

IPR2020-00464 filed Jan. 27, 2020

Inter Partes Review Certificate for:

Patent No.: 7,820,419
Issued: Oct. 26, 2010
Appl. No.: 11/814,304
Filed: Sep. 24, 2007

The results of IPR2020-00464 are reflected in this inter partes review certificate under 35 U.S.C. 318(b).

INTER PARTES REVIEW CERTIFICATE
U.S. Patent 7,820,419 K1
Trial No. IPR2020-00464
Certificate Issued May 10, 2023

AS A RESULT OF THE INTER PARTES REVIEW PROCEEDING, IT HAS BEEN DETERMINED THAT:

Claims 1-9, 11 and 13-19 are cancelled.

\* \* \* \* \*